US 6,677,430 B1

(12) United States Patent
Desjardins et al.

(10) Patent No.: US 6,677,430 B1
(45) Date of Patent: Jan. 13, 2004

(54) FLUORESCENT MOTILIN PEPTIDES

(75) Inventors: Clarissa Desjardins, Montreal (CA); Jacek Slon-Usakiewicz, Montreal (CA); Katherine J. Bonter, Montreal (CA)

(73) Assignee: Advanced Bioconcept Company, Montreal (CA)

( * ) Notice: Subject to any disclaimer, the term of this patent is extended or adjusted under 35 U.S.C. 154(b) by 0 days.

(21) Appl. No.: 09/539,593

(22) Filed: Mar. 31, 2000

Related U.S. Application Data

(63) Continuation-in-part of application No. 08/682,810, filed on Jul. 10, 1996, now Pat. No. 6,054,557, which is a continuation-in-part of application No. 08/504,856, filed on Jul. 20, 1995, now abandoned.

(51) Int. Cl.[7] ............................. C07K 5/00; C07K 7/00; C07K 16/00; C07K 17/00
(52) U.S. Cl. ..................... 530/324; 530/350; 435/7.1
(58) Field of Search ............................. 530/350, 324; 435/7.1

(56) References Cited

U.S. PATENT DOCUMENTS

| | | | |
|---|---|---|---|
| 4,046,633 A | 9/1977 | Keutel | 195/103.5 R |
| 5,187,288 A | 2/1993 | Kang et al. | 548/110 |
| 5,248,782 A | 9/1993 | Haugland et al. | 548/110 |
| 5,274,113 A | 12/1993 | Kang et al. | 548/405 |

FOREIGN PATENT DOCUMENTS

| | | |
|---|---|---|
| DE | 27 02 699 A1 | 12/1977 |
| DE | 3912046 A1 | 3/1990 |
| EP | 0 007 407 | 2/1980 |
| EP | 0 240 914 A2 | 10/1987 |
| EP | 0 331 126 A2 | 9/1989 |
| EP | 0 466 565 A1 | 1/1992 |
| EP | 0 606 804 | 7/1994 |
| EP | 0 608 987 | 8/1994 |
| GB | 2 291 708 A | 3/1996 |
| WO | WO 93/04194 | 3/1993 |
| WO | WO 93/18068 | 9/1993 |
| WO | WO 95/22341 | 8/1995 |
| WO | WO 96/31531 | 10/1996 |
| WO | WO 97/04311 | 2/1997 |
| WO | WO 98/05962 | 12/1998 |

OTHER PUBLICATIONS

Alcade et al., "Study of the Binding of Motilin to the Membranes of Enterocytes From Rabbit Jejunum," *Peptides*, 17(7):1237–1241 (1996).

Amoscato et al., "Synthesis of Two Biologically Active Fluorescent Probes of Thymopentin" *Peptide Protein Res.*, 29:177–186 (1987).

(List continued on next page.)

*Primary Examiner*—Dwayne C. Jones
*Assistant Examiner*—C. Delacroix-Muirheid
(74) *Attorney, Agent, or Firm*—Iandiorio & Teska

(57) ABSTRACT

Light emitting compounds of the formula:

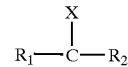

where $R_1$ is a light-emitting moiety and $R_2$ is a motilin peptide and fragment, derivative or analog thereof The peptide is linked at a first amino acid position to (C—X) which, in turn, is selected from the group including C=O, C=S, CH(OH), C=C=O, C=NH, CH$_2$, CH(OR), CH(NR), CH(R), CR$_3$R$_4$, and C(OR$_3$)OR$_4$ where R, R$_3$, and R$_4$ are alkyl moieties or substituted alkyl moieties. Optionally the compound may include a linker moiety between the peptide and the C—X binding group. Preferably, the compound exhibits substantial biological activity in the presence of receptors having affinities for motilin peptides.

21 Claims, 2 Drawing Sheets

OTHER PUBLICATIONS

Ashworth et al., "Visualization of the Thyropoin–releasing Hormone Receptor And Its Ligand During Endocytosis And Recycling" *Proc. Nat'l. Acad. Sci. USA*, 92:512–516 (1995).

Beaudet et al., "Annales d'endocrinologie" p. L14, Sep. 1–3, 1994 (conference date).

Bechtol et al., "Using Dyes and Filters in a Fluorescent Imaging System" *American Biotechnology Laboratory*, 8–10 (1994).

Cardullo et al., "Speract Receptors Are Localized on Sea Urchin Sperm Flagella Using a Fluorescent Peptide Analog" *Developmental Biology*, 162:600–607 (1994).

Chard, Laboratory Techniques in Biochemistry and Molecular Biology, Elsevier Biomedical Press, New York. 1996.

Cheng et al., "Fluorescent Rhodamine–Labeled Thyroid Hormone Derivatives" *FEBS Letters*, 100:113–116 (1979).

Cheng et al., "Receptor–mediated Uptake Of 3,3'5–tri-iodo–L–thyronine By Cultured Fibroblasts" *Proc. Nat'l. Acad. Sci. USA*, 77:3425–3429 (1980).

Chersi et al., "Preparation And Utilization Of Fluorescent Synthetic Peptides" *Biochemica et Biophysica Acta*, 1034:333–336 (1990).

Cushman, "Spectrophotometric Assay And Properties Of the Angiotensin–converting Enzyme of Rabbit Lung" *Biochemical Pharmacology*, 20:1637–1648 (1971).

Depoortere et al., "Demonstration and characterization of motilin–binding sites in the rabbit cerebellum," *Am. J. Physiol.*, 272:G994–G999 (1997).

Haugland, *Handbook of Fluorescent Probes and Research Chemicals—5$^{th}$ edition* (1992–1994).

Lee et al., "Effect of rabbit antimotilin serum on myoelectric activity and plasma motilin concentration in fasting dog," *Am. J. Physiol.*, 245:G547–G553, (1983).

Macielag et al., "Synthesis and characterization of site–specific biotinylated probes for the motilin receptor," *Int. J. Peptide Protein Research*, 44(6):582–588, (1994).

Macielag et al., "Synthesis and in vitro evaluation of [Leu13] orcine motilin fragments," *Peptides*, 13:565–569 (1992).

Maxfield, "Flourescent Analogs Of Peptides And Hormones" *Methods in Cell Biology*, 29:13–28 (1989).

Miller et al., "Structure–Function Studies of Motilin Analogues," *Peptides*, 16(1):11–18 (1995).

Niedel et al., "Receptor–mediated Internalization of Fluorescent Chemotactic Peptide By Human Neutrophils" *Science*, 205:1412–1414 (1979).

Poitras et al., "Heterogeneity of Motilin Receptors in the Gastrointestinal Tract of the Rabbit," *Peptides*, 17(4):701–707 (1996).

Roettger, et al., "Insulation Of A G Protein–coupled Receptor On the Plasmalemmal Surface Of the Pancreatic Acinar Cell" *J. Cell Biol.*, 130:579–590 (1995).

Rubanyi et al., "Endothelins: Molecular Biology, Biochemistry, Pharmacology, Physiology, And Pathophysiology" *Pharmacological Reviews*, 46:325–415 (1994).

Sack et al., "Cell Type–specific Binding of Ricinus Lectin To Murine Cerebellar Cell Surfaces In Vitro" *Cell Tissue Research*, 228:183–204 (1983).

Scarpignato et al., "Management of irritable bowel syndrome: Novel approaches to the pharmacology of gut motility," *Can. J. Gastroenterol.* 13(A):50A–65A, (1999).

Schaffer et al., "Fluorescence–activated Cell Sorting Of Embryonic Mouse and Rat Motoneurons and Their Long–term Survival In Vitro" *J. of Neuroscience*, 7:3088–3104 (1987).

Schecter et al., "Fluorescent Labeling of Hormone Receptors In Viable Cells: Preparation And Properties Of Highly Fluorescent Derivatives of Epidermal Growth Factor and Insulin" *Proc. Nat'l Acad. Sci. USA*, 75:2135–2139 (1978).

Sigma Immuno Chemicals Company, FluoroTag FITC Conjugation Kit (1994).

St. John et al., "Analysis and Isolation of Embryonic Mammalian Neurons By Fluorescence–Activated Cell Sorting" *Journal of Neuroscience*, 6:1492–1512 (1986).

Taylor and Wang, "Fluorescently Labelled Molecules As Probes of the Structure And Function Of Living Cells" *Nature*, 284:405–410 (1980).

Usellini et al., "Ultrastructural localization of motilin in endocrine cells of human and dog intestine by the immunogold technique," *Histochem.*, 81:363–368 (1984).

Zhao, "Attachment Of A Single Fluorescent Label To Peptides For Determination By Capillary Zone Electrophoresis" *Journal of Chromatography*, 608:239–242 (1992).

|  | EC50 | KI |
|---|---|---|
| ● Motilin | 5.00e-010 | 2.50e-010 |
| △ MTL011 URK4A | 1.10e-009 | 5.50e-010 |

|  | EC50 | KI |
|---|---|---|
| ● Motilin porcine | 6.00e-010 | 2.90e-010 |
| △ MOT741-YTJ4A | 5.20e-009 | 2.50e-009 |

FLUORESCENT MOTILIN PEPTIDES

CROSS REFERENCE TO RELATED APPLICATIONS

This application is a continuation-in-part application of U.S. Ser. No. 08/682,810 filed Jul. 10, 1996 entitled "Fluorescent Peptides", and now U.S. Pat. No. 6,054,557 which is a continuation-in-part application of U.S. Ser. No. 08/504,856, having the same name and filed Jul. 20, 1995 now abandon, which are hereby incorporated in their entirety by reference.

BACKGROUND OF THE INVENTION

This invention relates to peptide-based compounds having light-emitting moieties. Peptides may be chemically linked with detectable "labels" and used as probes, for example, to monitor peptide, cytokine, drug, and hormone receptors at the cellular level. Typically, the labeled peptide is placed in contact with a tissue or cell culture where it binds to an available receptor. Once bound, the label is detected, allowing properties such as receptor distribution or receptor binding kinetics to be monitored.

Peptides are typically labeled with radioactive elements such as $^{125}$I or $^{3}$H. In this case, emission of high-energy radioactive particles is monitored using standard γ-ray detectors, thereby allowing detection of the label. While detection techniques for $^{125}$I and $^{3}$H are well-known, radioactive compounds by nature have limited half lives, and are often both toxic and expensive. Moreover, current detection technology makes it difficult or impossible to detect radioactive probes in real-time, thereby precluding study of kinetic processes.

Peptides labeled with non-radioactive molecules have also been disclosed. Macielag et al. (*Int. J. Pept. Protein Res.* (1994) 44(6):582–588)) discloses a biotin-labeled motilin peptide. However, detection of this biotin-labeled motilin peptide requires and multiple assay steps.

Motilin is a 22-amino acid polypeptide secreted from the endocrine cells of the mucosa of the upper part of the small intestine. Motilin binds to G-coupled receptors to stimulate peristaltic contractions of the stomach and small intestine during fasting (Lee et al., *Am. J. Physiol.* (1983) 245G547-G553; Poitras , P. *Gastroenterology* (1984) 87:909–913; Scarpignato et al, *Can. J. Gastroenter.* (1999) 13(A): 50A–65A; Usellin et al., *Histochemistry* (1984) 81:363–368). There is also evidence that suggests motilin and motilin receptors are present in the brain and have a role in the regulation of food intake (Asakawa et al., *Peptides* (1998) 19(6):987–990).

Motilin's wide tissue distribution makes it a particularly desirable peptide to label and use to monitor cell receptors, as these peptides exhibit multiple biological roles and their receptors are located in a variety of tissues. Labeled motilin polypeptides are valuable in the identification of agonists and antagonist of motilin which may be useful as appetite stimulants or in the treatment of digestive disorders, for example, hypokinetic and hyperkinetic digestive disorders, such as irritable bowel syndrome associated constipation or diarrhea, or Chron's disease.

There exists the need for peptides that are chemically linked to detectable labels that are easily detected, yet do not decrease the biological activity of the peptide.

SUMMARY OF THE INVENTION

The present invention provides a compound containing a motilin peptide and a light-emitting moiety that is both biologically active and optically detectable. The peptide is chemically attached to the light-emitting moiety at an amino acid position that is not involved in binding to the peptide receptor. In this way, the peptide's affinity for the binding site is not significantly decreased and the compound retains high biological activity. Furthermore, the compound can be easily detected using standard optical means.

In general, in one aspect, the invention provides a biologically active compound of the formula:

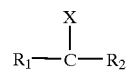

where $R_1$ is a light-emitting moiety and $R_2$ is a motilin peptide, fragment, derivative or analog thereof The peptide is linked at a first amino acid position to (C—X) which, in turn, is selected from the group including C=O, C=S, CH(OH), C=C=O, C=NH, $CH_2$, CH(OR), CH(NR), CH(R), $CR_3R_4$, and $C(OR_3)OR_4$ where R, $R_3$, and $R_4$ are alkyl moieties or substituted alkyl moieties. Optionally the compound may include a linker moiety between the peptide and the C—X binding group. Preferably, the compound exhibits substantial biological activity in the presence of receptors having affinities for motilin peptides. The compound may also be in the form of a pharmaceutically acceptable salt or complex thereof. Preferably, one of the C-terminal eight residues of the motilin peptide of SEQ ID NO:1(referred to herein is the C-terminal octapeptide) that is not required for motilin receptor binding or stability is attached to (C—X), either directly or through a linker moiety (Macielag et al., supra).

In preferred embodiments, the motilin peptide can be any peptide that shares sufficient homology with SEQ ID NO:1, Phe-Val-Pro-Ile-Phe-Thr-Tyr-Gly-Glu-Leu-Gln-Arg-Met-Gln-Glu-Lys-Glu-Arg-Asn-Lys-Gly-Gln or a fragment, derivative, or analog thereof. In particularly preferred embodiments, motilin peptides homologs, such as the canine motilin SEQ ID NO:2, Phe-Val-Pro-Ile-Phe-Thr-His-Ser-Glu-Leu-Gln-Lys-Ile-Arg-Glu-Lys-Glu-Arg-Asn-Lys-Gly-Gly (MW 2685) and porcine motilin SEQ ID NO:3, Phe-Val-Pro-Ile-Phe-Thr-Tyr-Gly-Glu-Leu-Gln-Arg-Met-Gln-Glu-Lys-Glu-Arg-Asn-Lys-Gly-Gln (MW 2697) may be used as motilin peptides in the present invention. Alternatively, the motilin peptide could be a modified motilin peptide that includes various substitutions or contains modified amino acids, such as beta-alanine or norleucine and the like. In preferred embodiments, any one of the eight residues of the C-terminal octapeptide of motilin is preferably chemically bound to the (C—X) moiety of the present invention. In one preferred embodiment, the motilin peptide is chemically bound to the (C—X) moiety through Lys$^{20}$. In a particularly preferred embodiment, the peptide is attached to the (C—X) moiety through Lys$^{20}$ and the (C—X) bond is preferably either C=O or C=S. In yet another preferred embodiment, the peptide may be amidated at the C-terminus.

In other preferred embodiments, the light-emitting moiety ($R_1$) is selected from the group including 4,4-difluoro-4-bora-3a,4a-diaza-s-indacene (e.g., 6-((4,4-difluoro-1,3-dimethyl-5-(4-methoxyphenyl)-4-bora-3a,4a-diaza-s-indacene-2-propionyl)amino) hexanoic acid) (BODIPY® TMR) or 4,4-difluoro-5-(2-pyrrolyl)-4-bora-3a,4a-diaza-s-indacene-3-propionic acid (BODIPY® 576/589)), fluorescein, fluorescein isothiocynate (FITC, Texas red, phycoerythrin, rhodamine, carboxytetramethylrhodamine, indopyras dyes, Cascade blue, coumarins, nitrobenzo-2-oxadiazole (NBD), Lucifer Yellow, propidium iodide, CY3, CY5, CY9, dinitrophenol (DNP), lanthanide cryptates, lanthanide chelates, non-fluorescent dialdehydes (OPA, NDA, ADA, ATTOTAG reagents from Molecular Probes) which react with primary amines (N-term lys) in the presence of a nucleophile (i.e. CN) to form fluorescent isoindoles, dansyl dyes fluorescamine and dabcyl chloride, 5-((((2-iodoacetyl)amino)ethyl)amino) naphthalene-1-sulfonic acid, long lifetime dyes comprised of metal-ligand complexes (MLC) which consist of a metal center (Ru, Re, Os) and organic or inorganic ligands complexed to the metal such as [Ru(bpy)$_3$]$^{2+}$ and [Ru(bpy)$_2$(dcbpy)], and the like and derivatives thereof. The light-emitting moiety can be attached to the peptide by reaction of a reactive side group (of a light-emitting molecule) with any C-terminal eight residues of the motilin peptide. Suitable reactive side groups include, by way of example only, indoacetamide, maleimide, isothiocyanate, succinimidyl ester, sulfonyl halide, aldehydes, glyoxal, hydrazine and derivatives thereof.

The above-identified compound is useful in the labeling of cell receptor sites, cell sorting, flow cytometry and performing fluoroimmunoassays. In another aspect, the invention provides a method for labeling a receptor having an affinity for a motilin peptide by contacting the receptor with one or more of the compounds described above. Cell receptor sites, can be imaged by contacting candidate cell receptor sites with the compound of the invention, and then detecting the bound compounds as an indication of the cell receptor sites. Cell sorting can be performed by contacting a population of cells with compound and isolating cells bound to the compound. Flow cytometry can be performed by contacting a population of cells with the compound and detecting cells bearing receptors on their surfaces by detecting cells bound to the compound. In other preferred embodiments it is possible to use the compound to label receptor sites on a model organism (e.g., *C. elegans*) in order to elucidate the tissue distribution of the receptor sites.

The invention has many advantages. In a general sense, peptide-containing compounds which retain their biological activity after being labeled with light-emitting moieties have a wide variety of biological applications. Such compounds can be used to identify, visualize, quantify, target, and select receptors on cells and tissues both in vitro and in vivo. These compounds may be used in place of more conventionally labeled peptides, such a $^{125}$I radiolabeled peptides. Radiolabeled compounds are often toxic, environmentally hazardous, chemically unstable and have, by the nature of the radioactive decay rate, relatively short lifetimes. In contrast, fluorescently-labeled motilin peptides are relatively safe and non-toxic, thereby allowing it to be synthesized and used without employing special laboratory procedures. Similarly, following use, fluorescent motilin peptides may be easily disposed, whereas disposal of radioactive compounds is both time-consuming and costly. In addition, fluorescent markers for motilin peptide receptors are stable and may be stored for extensive periods of time without undergoing considerable degradation.

Use of motilin peptides in the labeled compound provides several additional advantages. As described above, motilin peptides exhibit biological activity in tissues such as the brain and the gastrointestinal tract, and are involved in the regulation of gastrointestinal motor activity during fasting. Therefore, motilin peptides may be used as probes to investigate a number of different cell types. In addition, the motilin peptide has a relatively simple structure (10–27 amino acids) and can be synthesized and isolated with standard, well-known techniques.

During typical experiments, fluorescent markers for motilin receptors emit optical signals, and thus may be monitored by eye or with the aid of external optical detectors. In this way, the fluorescent peptides obviate the need for secondary detection steps sometimes used for radiolabeled compounds or incubation with secondary labeled compounds. Detection of optical radiation is, in general, relatively simple and cost-effective compared to detection of radioactive particles (e.g., α-particles); conventional charge-coupled device (CCDs) or light-sensitive cameras can therefore be used without modification for this application.

In addition, because of their high optical emission rates and well-characterized emission cross sections, fluorescent markers attached to motilin peptides can be used for real-time, quantified imaging of a number of dynamic biological phenomena, such as kinetics associated with receptor binding. The compounds can also be used for static processes, such as monitoring peptide distribution within a cell. Motilin peptide receptors marked with fluorescent markers may also be used in flow cytometry, confocal microscopy, fluorescence polarization spectroscopy, and any other techniques exploiting the optical detection of fluorescence or photoluminescence.

In a related aspect the present invention provides an assay method for evaluating a known or candidate motilin peptide for receptor binding that involves bringing together a molecule, the labeled motilin compound of the invention, and a motilin receptor preparation containing motilin receptors capable of detectably binding motilin, and determining or measuring the ability of the molecule to compete against the compound for binding to the motilin receptor preparation. A similar assay method is provided by the invention for determining the presence or amount of a motilin receptor binding molecule in a test sample that includes the steps of a) bringing together the test sample and a motilin receptor preparation containing motilin receptors capable of detectably binding motilin; b) measuring the ability of the test sample to compete against the labeled motilin compound the invention for binding to the motilin receptor preparation; and c) optionally comparing the amount of motilin receptor binding molecule in the test sample to the amount of motilin receptor binding in a control sample.

In another related aspect, the invention provides an assay method for screening cell lines, cells desegregated from tissue, or cell membrane preparations, to identify those cells that carry motilin, that involves a) contacting test cells or cell membrane preparations with the labeled motilin compound of the invention, and b) detecting an increase in fluorescent signal on the cell compared to a control, an increase in fluorescent signal indicating that a motilin receptor is present in the cell.

In a final aspect, the invention provides a kit for identifying natural and non-natural molecules that bind to the human motilin receptor, for use in treating motilin-related disease that includes a) at least one of the labeled motilin compounds of the invention; and b) a receptacle containing a human motilin receptor preparation. Optionally, the kit further includes instructions for utilizing the reagents in (a) and (b) in fluorescence assays to identify the molecules.

Other advantages and features of the invention will become apparent from the following detailed description, and from the claims.

DEFINITIONS

"Motilin peptide": "Motilin peptide" In preferred embodiments, the motilin peptide can be any peptide that shares sufficient homology with motilin (SEQ ID NO:1). In particularly preferred embodiments, the motilin peptide is the canine (SEQ ID NO:2) or porcine (SEQ ID NO:3) motilin peptide. For example, any peptide with substantial homology and biological activity similar to motilin, as determined by one of ordinary skill in the art, would be considered to qualify as a motilin peptide. For example, according to the present invention, a motilin peptide has preferably 60% amino acid identity to motilin, more preferably, 80% amino acid identity, most preferably, 90% amino acid identity over a span of at least 10 amino acids. Preferably, the motilin peptide or "motilin compound" includes fragments of motilin, derivatives, or analogs thereof. Motilin peptides may be peptides whose sequences differ from motilin's wild-type sequence by only conservative amino acid substitutions. For example, one amino acid may be substituted for another with similar characteristics (e.g., valine for glycine, arginine for lysine, etc.) or by one or more non-conservative amino acid substitutions, deletions, or insertions which do not abolish the peptide's biological activity. Alternatively, the motilin peptide could be a modified motilin peptide that includes various substitutions or contains modified amino acids, such as beta-alanine or norleucine and the like. Other useful modifications include those which increase motilin's stability. The peptide may contain, for example, one or more non-peptide bonds (which replace a corresponding peptide bond) or D-amino acids in the peptide sequence. Additionally, the C-terminus carboxylic acid group may be modified to increase peptide stability. For example, as described above, the C-terminus may be amidated or otherwise derivatized to reduce the peptide susceptibility to degradation.

"Receptor": As referred to herein, the term "receptor" or "motilin receptor" refers to a macromolecule capable of recognizing and specifically binding with a motilin ligand, and which after binding, is capable of stimulating or suppressing the physical or chemical signal that initiates the chain of events leading to a physiological response from that receptor (Blecher et al. "Receptors and Human Disease," Williams & Wilkins, Baltimore, 1981, Chapter 1). It is thus an important part of this invention that the tissues, cells, membranes, and recombinant receptor preparations used in the present invention exhibit the binding characteristics of a natural receptor.

The term "natural" may also be use to refer to a molecule to differentiate a natural molecule from a synthetic molecule (i.e., a recombinant molecule). Essentially, "natural" means occurring in nature.

"Fluorescent peptide" or "compound": As referred to herein, "fluorescent peptide" or "compound" refers to a peptide-based compound that has been labeled with a light emitting moiety. The fluorescent peptide has the desirable characteristics of preserving the biological activity of the peptide-based compound, for example in receptor binding, and providing a detectable signal that can be measured using standard optical means.

"Light emitting molecule": "Light emitting molecule," as used herein, refers to a molecule capable of emitting light of any detectable wavelength that is not attached to a peptide of the present invention and may include a reactive side chain for coupling with a motilin peptide.

"Light emitting moiety": "Light emitting moiety" is used to refer to a light emitting molecule (e.g., a fluorescent dye) that has been attached by any of a variety of means, as described below, to peptide-based moiety. Attachment to the peptide-based moiety is carried out so that the biological activity of the peptide-based moiety is maintained. The light emitting moiety provides a detectable signal of a particular wavelength. In general, the signal provided by light emitting moieties may be detected by a variety of techniques including conventional microscopy methods, including fluorescence or confocal microscopy, atomic force microscopy, fluorescence polarization spectroscopy and fluorimetry. Particularly preferred light emitting moieties are described in more detail below.

"Peptide moiety": "Peptide moiety", as used herein, refers to any peptide composed of any sequence of natural and/or custom amino acids. By "custom amino acid" is meant any amino acid that cannot be found in nature, but can be synthesized in a laboratory. Such amino acids are often chemically modified amino acids. It is well known that natural amino acids may also be synthesized. Particularly preferred peptide moieties of the present invention include motilin peptides. Most particularly preferred are the canine and porcine motilin peptides or fragments, derivatives, or analogs thereof.

"Linker moiety" or "linker": A "linker moiety" or "linker" is any moiety of the compound located between the peptide and the label or at any other position which provides greater three dimensional separation between the label and the peptide. Moieties that may be used as linkers in the present invention include those derived from glycine, γ-aminobutyric acid, beta-alanine, aminopentanoic acid, aminohexanoic acid, aminohepanoic acid, aminooctanoic acid, aminononanoic acid, aminodecanoic acid, aminoundecanoic acid, and aminododecanoic acid. Each of these moieties include an amino and a carboxylic acid functionality and so may be incorporated into the compound using a peptide bond.

"Biologically active compound" or "biologically active peptide": "Biologically active compound" or "biologically active peptide", as used herein, refers to the fluorescently labeled peptide of the invention represented in the formula described below and in FIG. 1. Any biologically active compound of the present invention is substantially biologically active.

"Substantially biologically active": In all cases, by "substantially biologically active" is meant that the compound binds to a receptor having an affinity $IC_{50}$ or $K_i$ value for the compound which is no more than 100 times, preferably no more than 15 times, more preferably no more than 10 times and most preferably equal to or less than that of the corresponding unlabeled peptide. Most preferably, an affinity $IC_{50}$ or $K_i$ value for the compound is no more than 10 nM. Receptor affinity in this case can be determined using known methods, such as methods involving competitive binding of radioactively labeled peptides or by using known methods of fluorescence polarization or other known fluorescence technique for measuring the $K_d$ for the receptor/peptide interaction.

"Low" or "no" biological activity or "biologically inactive": By "low" or "no" biological activity or "biologically inactive" is meant biological activities less than 0.25% of the biological activity of $R_2$—H in the presence of a receptor having affinity for motilin peptides.

"Motilin-related disease": By "motilin-related disease" is meant a disease that is at least in part caused by a defect in motilin activity (e.g., motilin receptor binding).

DETAILED DESCRIPTION OF THE INVENTION

Figure 1:
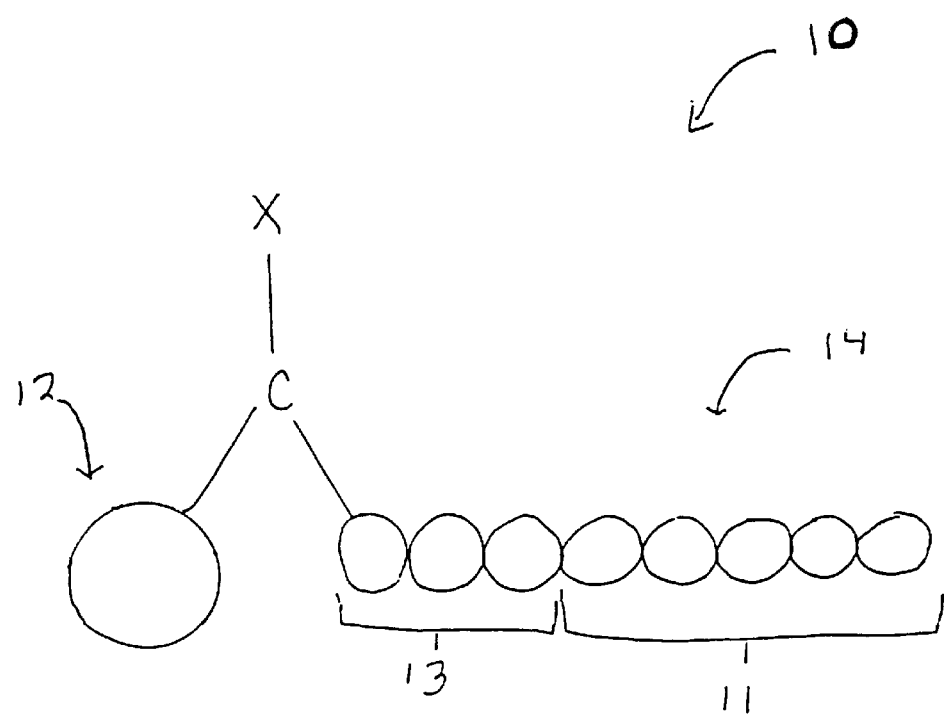
FIG. 1 is a schematic drawing of the chemical structure of fluorescently-labeled motilin peptide according to the invention.

The present invention provides biologically active labeled peptides that can be used in a variety of assays including labeling recombinant cells, labeling cultured cells, labeling tissue sections, labeling live tissue by injection to a particular site. Labeling can also be detected directly by confocal microscopy, fluorescence polarization, or flow cytometry. In one preferred embodiment, (FIG. 1), a fluorescent peptide 10 according to the invention includes a light-emitting moiety 12, such as a fluorescent dye, linked via a (CX) bond to a peptide moiety 14. The peptide moiety 14 includes amino acid residues of a motilin peptide, and fragments, derivatives or analogs thereof.

In one preferred embodiment, in order to retain substantial biological activity and affinity for motilin peptide receptors, the peptide is attached to a fluorescent label via the (CX) linking moiety at an amino acid bound to one of the eight residues in the C-terminal octapeptide of motilin (SEQ ID NO:1). In general, the C-terminal octapeptide is not critical for the full biological activity of motilin peptides, i.e., it is not significantly involved in motilin receptor binding or in stabilizing the bioactive conformation (Macielag et al., *Peptides* (1992) 13:565–569). Therefore, if placed at any of the residues in the C-terminal octapeptide, the light-emitting moiety may not sterically hinder or otherwise significantly affect the region involved in receptor binding, and the biological activity of the compound is thus maintained. For example, in one particularly preferred embodiment, the peptide is attached to a fluorescent label via the (CX) linking moiety at Lys$^{20}$ (position 20) of the motilin peptide of SEQ ID NO:1. The light-emitting moiety may be covalently bonded to the (CX) linking group at any available position. The (CX) linking group represents the bond formed between the light-emitting moiety and the peptide upon reaction and this bond may include groups such as C=O, C=S, CH(OH), C=C=O, C=NH, CH$_2$, CH(OR), CH(NR), CH(R), CR$_3$R$_4$, and C(OR$_3$)OR$_4$ where R, R$_3$, and R$_4$ are alkyl moieties or substituted alkyl moieties.

Fluorescent peptides of this type have amino acids which are available for binding to motilin peptide-recognizing receptors, thereby enabling the fluorescent peptide to be used for labeling purposes. Once the fluorescent peptide is bound to an available receptor, the attached light-emitting moiety retains optical properties similar to those of an unbound light-emitting molecule. In this way, the fluorescent peptide can bind to the corresponding receptor and emit light following absorption of an incident optical field, and thus serve as a marker for the motilin peptide receptor. This allows the receptor to be "labeled" and permits investigation, for example, of peptide/receptor interactions. In particular, fluorescently labeled peptides participating in receptor/peptide interactions can be monitored to determine the location of receptors in cell or tissue samples, and additionally allow quantification of receptors, determination of the receptor affinity for various ligands, or the identification of various populations of cells.

In alternative embodiments of the present invention, a linker moiety may be used to provide greater three dimensional separation between the label and the peptide and to attach the peptide to the fluorescein label.

The invention provides labeled peptides that retain their biological activity. In certain preferred embodiments of the invention, the combined practice of 1) attaching the label to a region of the peptide that is not essential for the biological activity of the peptide; and 2) providing a linker between the label and the peptide, when necessary, may facilitate maintenance of the biological activity of the peptide. Preferably, the linker is chemically similar to an amino acid and is capable of forming peptide bonds with the motilin peptide. A variety of linkers are known in the art that may be used in the present invention. For example, glycine, beta-alanine, aminopentanoic acid, aminohexanoic acid, aminohepanoic acid, aminooctanoic acid, aminononanoic acid, aminodecanoic acid, aminoundecanoic acid, aminododecanoic acid and β-(2-naphthyl)-L-alanine.

Motilin peptides may be synthesized using techniques known in the art, extracted from natural systems, or obtained from commercial sources (e.g., American Peptide, Peninsula, Neosystems, Sigma, BASF). A list of the motilin peptides referred to herein and their analogs that may be used to practice the invention may be obtained from American Peptide Co., Inc product catalogue. Typically, the peptide is either purchased or synthesized using conventional solid-phase synthetic techniques. Preferably, the peptide is substantially pure, meaning that it is at least 60% by weight free from the other compounds with which it is naturally associated.

Once the desired peptide is obtained, fluorescent peptides having high biological activities are made by attaching the light-emitting moiety to motilin peptide moiety, preferably to one of the residues of the C-terminal octapeptide of SEQ ID NO:1, or fragment, derivative, or analog thereof, most preferably to the twentieth amino acid position of the motilin peptide moiety of SEQ ID NO:1. In general, this reaction is carried out by modifying a functional group on the peptide, most typically a thiol or amine group, so that this peptide moiety may be easily attached to the light-emitting moiety. Reactions for such modifications are described in, for example, "*Handbook of Fluorescent Probes and Research Chemicals-5th Edition*" (supra).

The conditions used to modify amine moieties of the desired peptide will depend on the class of amine (e.g., aromatic, aliphatic) and its basicity. Aliphatic amines, such as the α-amino acid groups of lysine and arginine, are moderately basic and reactive with acylating reagents. The concentrations of the free base form of the aliphatic amines below pH 8 is very low; thus, the kinetics of acylation reaction of amines by isothiocyanates, succinimidyl esters, and other reagents is strongly pH-dependent. Although amine acylation reactions should usually be carried out above pH 8.5, the acylation reagents degrade in the presence of water, with the rate increasing as the pH increases. Therefore, a pH of 8.5–9.5 is usually optimal.

In general, thiols or alcohols react with alkylating groups (R'—Z) to yield relatively stable ethers or thiol ethers (R'—S—R), e.g., (C—X) is the α-carbon of R', with the leaving group Z preferably being a halogen (e.g., Cl, Br, I) and the like. In particular, the most common reagents for derivatization of thiols are haloacetyl derivatives. Reaction of these reagents with thiols proceeds rapidly at or below room temperature in the physiological pH range.

In general, any dye, porphyrin, fluorophore, or other light-emitting molecule may be complexed with molitin peptide. In preferred embodiments, the light-emitting moiety is selected from the group including 4,4-difluoro-4-bora-3a,4a-diaza-s-indacene (e.g., 6-((4,4-difluoro-1,3-dimethyl-5-(4-methoxyphenyl)-4-bora-3a,4a-diaza-s-indacene-2-propionyl)amino) hexanoic acid), (BODIPY® TMR) or 4,4-difluoro-5-(2-pyrrolyl)-4-bora-3a,4a-diaza-s-indacene-3-propionic acid (BODIPY® 576/589)) fluorescein, FITC, Texas red, phycoerythrin, rhodamine, carboxytetramethylrhodamine, indopyras dyes, Cascade blue, coumarins, NBD, Lucifer Yellow, propidium iodide, CY3, CY5, CY9, dinitrophenol (DNP), lanthanide cryptates, lanthanide chelates, non-fluorescent dialdehydes (OPA, NDA, ADA, ATTOTAG reagents from Molecular Probes) which react with primary amines (N-term lysine) in the presence of a nucleophile (i.e. CN) to form fluorescent isoindoles, dansyl dyes, fluorescamine and dabcyl chloride, 5-((((2-iodoacetyl)amino)ethyl)amino) naphthalene-1-sulfonic acid, long lifetime dyes comprised of metal-ligand complexes (MLC) which consist of a metal center (Ru, Re, Os) and organic or inorganic ligands complexed to the metal such as $[Ru(bpy)_3]^{2+}$ and $[Ru(bpy)_2(dcbpy)]$, and the like and derivatives thereof. The synthesis and structures of several dyes which may be used are described in U.S. Pat. Nos. 5,248,782; 5,274,113; and 5,187,288, the contents of which are incorporated herein by reference. Other light-emitting moieties used in labeling or other applications may be attached to the peptide. For example, suitable light-emitting moieties are described in "Handbook of Fluorescent Probes and Research Chemicals-5th Edition" by Richard P. Haugland, 1994; and "Design and Application of Indicator Dyes", Noninvasive Techniques in Cell Biology: 1–20 by Richard P. Haugland et al., Wiley-Liss Inc. (1990), the contents of each of which is incorporated herein by reference.

In general, reactive groups on the light-emitting moiety, such as unsaturated alkyl groups or acylating moieties, will react with the modified peptide to form a dye/peptide bond. The chemical structure of the light-emitting moiety may affect the synthetic route used to synthesize the fluorescent motilin peptide analog. It may be necessary, for example, to modify the light-emitting moiety so that it includes a reactive group prior to exposing this moiety to the desired peptide. Such side groups may include indoacetamide, maleimide, isothiocyanate, succinimidyl ester, sulfonyl halide, aldehyde, glyoxal and hydrazine derivatives. Amino acids including alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine may be labeled according to the method described herein.

The chemistry used to synthesize the fluorescent peptide is not greatly dependent upon the exact structure of the motilin peptide analog. Thus, the general procedure outlined below may be used for most motilin peptides. Attachment of this peptide to a light-emitting moiety is described in detail in the Examples provided below.

Once synthesized, the resulting complex is purified, preferably using a column method such as high pressure liquid chromatography (HPLC), and then eluted. Collected fractions are then screened using analytical methods to determine if adequate biological activity is present. Fluorescent motilin peptide analogs having adequate biological activities are selected by first exposing these analogs to motilin peptide receptors; compounds binding effectively to these sites are then isolated from relatively inactive fluorescent peptides. In general, this selection process can be performed using standard techniques, such as column chromatography or other analytical techniques known in the art. The selection process is designed to allow maintenance of the compound's pharmacological binding, and thus allows only the dye/peptide compounds exhibiting substantial biological activities to be separated from relatively inactive compounds.

Figure 2A:
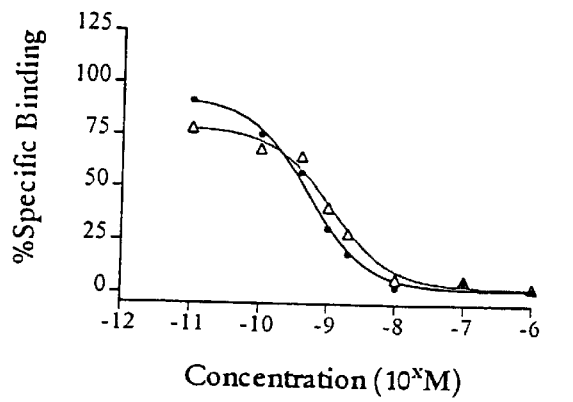
FIGS. 2(A and B) is a graph depicting displacement of $^{125}$I-motilin (NEX378) by motilin (procine), Fluorescein-motilin (MTL011 URK4A), (panel A), or 6-((4,4-difluoro-1,3-dimethyl-5-(4-methoxyphenyl)-4-bora-3a,4a-diaza-s-indacene-2-propionyl)amino) hexanoic acid-motilin (BODIPY® TMR-motilin) (MTL741-YTJ4A) (panel B).
Figure 2B:
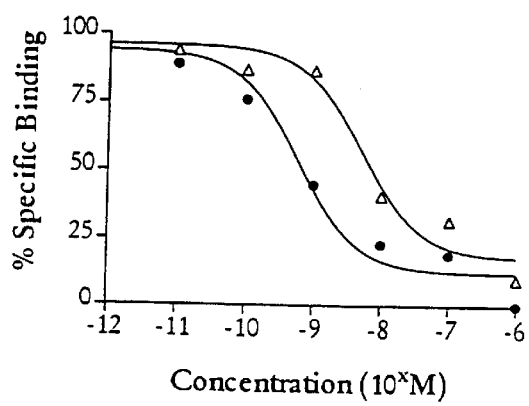

Displacement of a 6-((4,4-difluoro-1,3-dimethyl-5-(4-methoxyphenyl)-4-bora-3a,4a-diaza-s-indacene-2-propionyl)amino) hexanoic acid-motilin (BODIPY® TMR-motilin) peptide (MOT741) having the amino acid sequence Phe-Val-Pro-Ile-Phe-Thr-Tyr-Gly-Glu-Leu-Gln-Arg-Met-Gin-Glu-Lys-Glu-Arg-Asn-Lys-Gly-Gln (SEQ ID NO:1) by unlabeled canine and porcine motilin was used to measure the affinity of canine and porcine motilin for recombinant human motilin receptor sites (RB-HMOT, Receptor Biology, Inc., Beltsville, Md.) and to compare the displacement of the labeled 6-((4,4-difluoro-1,3-dimethyl-5-(4-methoxyphenyl)-4-bora-3a,4a-diaza-s-indacene-2-propionyl)amino) hexanoic acid-motilin (BODIPY® TMR-motilin) peptide to the unlabeled motilin peptides. The labeled compound exhibits dose-dependent binding to the human motilin receptor (RB-HMOT) comparable to canine and porcine motilin peptides, as determined by displacement of labeled-motilin peptides from the receptors. The $K_i$ values are 0.55 nM for Fluorescein-motilin and 2.5 nM for 6-((4,4-difluoro-1,3-dimethyl-5-(4-methoxyphenyl)-4-bora-3a,4a-diaza-s-indacene-2-propionyl)amino) hexanoic acid-motilin (BODIPY® TMR-motilin) as compared to 0.25 nM and 0.29 nM for unlabeled porcine motilin (FIG. 2). This demonstrates the high degree of retention of biological activity. The $IC_{50}$ is related to the binding constant $K_i$ by the formula $IC_{50}=K_i(1+F_L/K_d)$, where $F_L$ is the concentration of the free labeled ligand and $K_d$ is the dissociation constant for the labeled ligand. The $IC_{50}$ for canine motilin and porcine motilin is 16 nM and 4.5 nM respectively, compared to >1 μM for erythromycin. $IC_{50}$ and $K_i$ values such as those reported herein may be determined using techniques well-known in the art.

In addition, the binding of motilin (MOT741) to the human motilin receptor was monitored over time. The binding reached equilibrium in approximately 20 minutes and was stable for three hours. The bound signal started to decrease after three hours. At nine hours, the displaceable signal had been reduced by 57%.

In cases where it is not known which amino acid site may be complexed to form the fluorescent peptide of the invention, the peptide-fluorophore complexes may be screened to identify suitable complexes. The general synthetic method for identifying light-emitting, biologically active compounds of the invention is as follows.

The motilin peptide and the fluorophore of choice are incubated to form a mixture of compounds (i.e., fluorophore-labeled peptides). Incubation is performed under conditions which permit optimal peptide labeling. Typically, a solution containing the peptide at a concentration of about $10^{-2}$–$10^{-4}$ M is mixed with the light-emitting moiety in a highly basic solution, i.e., pH 9.3–10.7 such as a carbonate buffer, in at least a 1:4 peptide:light-emitting moiety molar ratio. The solution is mixed at room temperature for a time of between about 24 to 48 hours, and is protected from light and shaken periodically. The resulting mixture includes biologically active and inactive whole peptides, cleaved fragments of peptides, and singly and multiply labeled peptides.

After covalent bonding of the light-emitting moiety and the peptide occurs, unbound fluorophore is removed. In general, this step is performed using standard techniques such as column chromatography or other analytical techniques known in the art. In a typical example, unreacted amounts of the free fluorophore are removed using a G-50 column equilibrated with phosphate buffered saline (pH 7.4) and spun a 3000 rpm for a period of between 0.5 and 20 minutes. The resultant eluent contains a mixture of labeled biologically active and inactive peptides.

This solution is then collected and subjected to a high-stringency pharmacological binding assay. In this assay, only biologically active compounds are bound to tissue receptors; inactive compounds are washed away. The assay is typically performed on tissue sections, receptor-coated columns or membrane homogenates. In a typical example, an aliquot of the fluorescent peptide mixture is first dissolved in an aqueous solution (1:100) and incubated with an immobilized tissue sample containing high numbers of the peptide receptor, e.g., receptor transfected membrane homogenates. Alternatively, recombinant cells expressing a particular receptor may also be used as a membrane-bound receptor source.

The selection process is designed to separate compounds exhibiting substantial biological activity from those relatively inactive compounds. If necessary, during the assay, binding of the biologically active compounds may be rapidly observed visually, in a fluorometer or by using more sensitive techniques such as fluorescence polarization spectroscopy.

The receptor-bound compounds are then removed from the tissue surface or cell membrane and analyzed to identify the site at which the fluorophore is attached, i.e., the site allowing fluorophore attachment without interference with receptor binding. Biologically active compounds bound to membrane receptors are separated from the remaining inactive fluorescent peptides in solution, either by centrifugation of membrane homogenates (typically at 3000 rpm for about 5 minutes) or, in the case of tissue sections, by rapidly rinsing the sections in incubation buffer at 4° C. The membranes are then resuspended in binding buffer with the biologically active compound removed from the cell surfaces by incubation in a high salt/acid wash solution.

Once isolated, biologically active compounds are analyzed using known techniques, such as carboxypeptidase digestion and capillary electrophoresis, laser induced capillary zone electrophoresis, mass spectroscopy, and/or HPLC or amino acid sequencing, to identify the site of attachment between the light-emitting moiety and the peptide.

Applications

Fluorescent motilin compounds selected to have high biological activity have a number of uses. For most applications, the fluorescent compound is first contacted with the sample of interest. The compound is then incubated with the cells or tissues of the sample for a select time period and allowed to interact with the motilin peptide receptor. If necessary, excess, non-specifically bound compound may be washed away.

Once the peptide is bound to the desired receptor site, the labeled sample is imaged using standard techniques known in the art. Conventional microscopy methods, such as fluorescence or confocal microscopy, may be used to optically excite and then detect emission from the labeled receptors. Other imaging techniques which can be used with the fluorescent motilin peptide compounds include atomic force microscopy, fluorescence polarization spectroscopy, and fluorimetry.

Using the above techniques, small-scale features in the cell which normally would be difficult or impossible to detect are observed. For example, this allows visualization of intracellular receptor sites. Moreover, labeled peptides participating in peptide-receptor interactions can be monitored to determine the location of receptors, to determine receptor affinity for various unknown ligands (drug screening), and to identify various populations of cells endowed with peptide receptors. Optical radiation emitted from the fluorescing moiety can be easily and rapidly detected, allowing the fluorescent peptides to be used to monitor real-time receptor/peptide interactions. In this way, the compounds permit study of kinetic processes in the cell. Other applications include receptor sorting using FACS (fluorescence-associated cell sorting) and measurement of serum peptide levels using FIA (fluorescent immunoassays) either in vivo or in vitro for research or diagnostic purposes. In general, techniques which may utilize the compounds of the invention include, without limitation, flow cytometry, cell sorting (for example, top isolate populations of cells bearing a receptor of interest), tumor marking, fluorescent immunoassays, competitive binding assays for drug screening, and other in vitro experimental techniques involving compound labeling according to techniques known in the art.

More particularly, the invention provides rapid, inexpensive and physiological methods for identifying, screening and characterizing potential motilin agonists and antagonists for therapeutic usefulness, including assessing the ability of such candidate molecules to compete against tracer concentrations of certain labeled peptides, including certain labeled peptides, fragments, and analogs thereof, for binding to specific receptor binding sites in cells, on isolated membrane preparations, or from tissues containing cells with membrane receptors for motilin. Alternatively, preparations of recombinant motilin can be used in the assays of the present invention. For example, each well of a microtiter plate contains a constant amount of fluorescent ligand and membrane preparation containing the G-protein-coupled receptor of interest at quantities optimized based on the fluorescent properties of the bound and free fluorescent peptide. A test compound with an affinity for the G-protein-coupled receptor will displace receptor bound fluorescent peptide when added to the well. The magnitude of displacement reflects the potency of the potential drug and is quantified as a decrease in polarized emission of bound fluorescent peptide.

In one preferred embodiment, the invention provides an assay method for evaluating one or more receptor binding characteristics sought to be determined for a known or a candidate motilin agonist or antagonist molecule that includes the steps of 1) assessing or measuring the ability of the molecule to compete against a labeled ligand for binding to a motilin receptor preparation; and 2) determining the receptor binding characteristic sought to be determined for the molecule. Receptor binding characteristics which may be determined include binding affinity and binding specificity.

Specifically, the test samples which detectably bind to the motilin receptor protein are identified by measuring the displacement of a labeled first ligand from the receptor protein preparation by the test sample and comparing the measured displacement of the first labeled ligand from the receptor preparation by the test sample with the measured displacement of the labeled first ligand from the receptor preparation by one or more known second ligands. Labeled first ligands and second ligands include motilin, motilin agonists, and motilin antagonists. Useful receptor preparations include isolated cells bearing the motilin receptor, isolated membrane preparations bearing the motilin receptor, and isolated motilin receptor protein. When isolated membranes are used as the receptor preparation, especially preferred are membranes from the rat brain. Test samples used in any of the above methods that contain more than one test molecule and that yield positive results can then be divided and retested as many times as necessary or appropriate, to identify the molecule or molecules in the test sample that are responsible for yielding the positive result.

In another preferred embodiment, the invention provides an assay method for determining the presence or amount of a motilin receptor binding molecule in a test sample to be assayed that includes the steps of 1) bringing together the test sample and a motilin receptor preparation, 2) measuring the ability of the test sample to compete against a labeled ligand for binding to the motilin receptor preparation, and 3) relating the amount of motilin receptor binding molecule in the test sample with the amount of motilin receptor binding molecule measured for a control sample. A negative control sample, according to the invention may be a motilin receptor preparation known to lack any motilin receptor binding molecule. Alternatively, for a positive control, one could compare the amount of motilin receptor binding molecule in the test sample to the amount of motilin receptor binding molecule in a sample that contains a known amount of the labeled motilin compound. Alternatively, this assay method can be utilized to evaluate the potency of a motilin preparation and/or to evaluate the solubility characteristics of the motilin preparation.

In another preferred embodiment, the invention is used to screen cell lines, tissues, or cell membrane preparations, to identify those cells that contain motilin receptors. For example, test cells or cell membrane preparations may be contacted with the labeled compound of the invention and subsequently assayed to detect an increase in fluorescent signal compared to a negative control (i.e., a cell known to lack motilin receptors capable of detectably binding motilin), an increase in fluorescent signal indicating that a motilin receptor is present in the cell. Relative binding of the labeled compounds of the invention to the cell or membrane preparation may also be assessed by comparison to a positive control, for example, binding of the compound to a motilin receptor preparation containing motilin receptors capable of detectably binding motilin.

Lastly, the invention further provides a kit utilizing the methods listed above for identifying natural and non-natural motilin-receptor binding that may ultimately be used in treating motilin-related diseases. In preferred embodiments, the kit includes a receptacle containing a motilin receptor preparation and a receptacle containing fluorescently labeled motilin peptide capable of binding to the motilin receptor, preferably the human motilin receptor. Preferably, the kit further includes a buffer supplement for optimization of detection of fluorescent-peptide binding. Optionally, the kit further includes instructions for use for identifying motilin receptor binding molecules. For example, the instructions may indicate that the labeled motilin receptor is added to a solution containing motilin to form a peptide/receptor complex and further that the complex is then to be contacted with motilin competitors. The amount of labeled motilin displaced from the motilin receptor in the presence of competitor can then be assessed by methods standard in the art (i.e., Scatchard plat saturation analyses (Blecher 1976; Blecher 1981, Chapter 1; Boulton et al., 1986, Chapter 1; Bylund D. B., et al., "*Methods for Receptor Binding*," in H. I. Yamamura et al., eds., "*Methods in Neurotransmitter Analysis*," Raven Press, New York 1990 pp. 1–35), competition curves, wherein the amount of bound peptide is plotted as a function of the log of the concentration of ligand (Inplot program; Graph PAD Software, San Diego, Calif.; ALLFIT program of DeLean et al.; Munsun, U. and Robard, D., *Anal. Biochem.* (1980) 107:220–239).

The following Examples are used to more particularly point out the synthesis, selection methods, and use of fluorescent motilin peptide analogs having high biological activities.

EXAMPLE 1

Synthesis of Motilin Peptides

Peptides were synthesized using solid phase peptide synthesis methods either manually or automated (MPS396 peptides synthesizer, Advanced ChemTech). Coupling of amino acid residues was accomplished via Fmoc peptide synthesis chemistry (Fields, et al., 1990, IJPPR 35, 161). Syntheses were performed on Wang or on amide Rink resins, with side chain of amino acids fully protected. The reagents benzotriazol-1-yloxytris(dimethylamino)phosphonium hexafluorophosphate (BOP), (benzotriazol-1-yloxy) tripyrrolidinophosphonium hexafluorophosphate (PyBOP) or o-(benzotriazol-1-yl)-N,N,N',N'-tetramethyluronium tetrafluoroborate (TBTU) were used as activation agents depending on the chemistry and difficulty of the coupling reaction. All chemicals were purchased from Advanced ChemTech, Bachem and Calbiochem/NovaBiochem. Formation of each peptide bond between residues of the sequence was ensured by using a 3 to 6 fold excess of coupling reagents and by "double coupling"; meaning that the coupling reaction was repeated for each amino acid added to the growing peptide chain.

EXAMPLE 2

Labeling of Peptides

Labeling with Fluorescein

Synthesis using an orthogonal protection scheme made it possible to selectively deprotect Lys[20] of motilin and to label this position with the carboxylic form of fluorescein (Molecular Probes, Eugene, Oreg.). A 3-fold excess of fluorescein (0.05 mM) to peptide was dissolved in DMF and mixed with a resin (Fmoc-glutamine (TRT side chain protection) Wang resin from Applied Biosystems) for 24 hours. After 24 hours, the resin was washed ten times with DMF and three times with methanol/ethanol before the resin was air dried.

Labeling with BODIPY® dye (6-((4,4-difluoro-1,3-dimethyl-5-(4-methoxyphenyl)-4-bora-3a,4a-diaza-s-indacene-2-propionyl)amino) hexanoic acid (BODIPY® TMR) or 4,4-difluoro-5-(2-pyrrolyl)-4-bora-3a,4a-diaza-s-indacene-3-propionic acid (BODIPY® 576/589)).

After synthesis, the Fmoc-peptide was cleaved from the resin by mixing the resin with a solution of 0.25 ml EDT, 0.5 g phenol, 0.5 ml thioanisole, 0.5 ml of water, and 8.25 ml of trifluoroaceitc acid for two hours. The resin was filtered and washed three times with pure trifluroacetic acid (TFA) which cleaves the peptide from the resin. Excess TFA was partly evaporated and the peptide was precipitated in cold diethyl ether, dissolved in a 20–50% AcCN/water solution, and lyophilized. Analytical data of the crude product was obtained using analytical RP-HPLC and electrospray mass spectrometry (electrospray MS).

Specifically, the crude Fmoc-peptide was purified by HPLC on a Vydac C4 separative column (2.5×25 cm) with a linear gradient of 10–80% acetonitrile in water and 0.1% TFA over 80 minutes. The flow rate was 13 ml/min. Elution of the product was monitored by UV absorption at 215 nm. Analytical HPLC was then carried out on a Vydac C18 column (0.46×25 cm) with a linear gradient of 10–80% acetonitrile in water and 0.1% TFA over 80 minutes at a flow rate of 1 ml/min. Elution of product was monitored by UV absorption at 215 and/or 254 nm. Electrospray MS was used to estimate the purity of the fractions. The final product was obtained as a dry lyophilized powder with a purity greater than 95%, as estimated by analytical HPLC.

Subsequently, 5–7 mmol of the purified Fmoc-peptide was dissolved completely in 2 ml of N-methylpyrollidone (NMP), 5 mg of 4,4-difluoro-4-bora-3a,4a-diaza-s-indacene-ONSu (BODIPY®-ONSu, ONSu is the reactive group on BODIPY® dye that reacts with the $NH_2$ of the peptide), and 5 mg of the di-isopropyl ethylamine (iPr2EtN) and the reaction was incubated for three hours at room temperature. Crude labeled peptide was then applied to a semi-preparative HPLC column (as described above) without any preliminary treatment and eluted in 0.1% TFA with a linear gradient from 10 to 80% of $CH_3CN$ over 80 minutes. The molecular weight of the product was quantitated by electrospray MS. The molecular weight of (6-((4,4-difluoro-1,3-dimethyl-5-(4-methoxyphenyl)-4-bora-3a,4a-diaza-s-indacene-2-propionyl)amino) hexanoic acid-motilin (BODIPY® TMR-motilin) was 3193.2; 4,4-difluoro-5-(2-pyrrolyl)-4-bora-3a, 4a-diaza-s-indacene-3-propionic acid-motilin (BODIPY® 576/589-motilin) was 3010.5; and of Fluorescein labeled motilin was 3057.4.

Fmoc 44-difluoro-4-bora-3a,4a-diaza-s-indacene-peptide (Fmoc-BODIPY®), dried by lyophilization, was treated with 25% piperidine in dimethylformamide (DMF) over 20 minutes. The base was neutralized with 25% $CH_3COOH$ at 0° C. The peptide was purified on a semi-preparative HPLC column, as described above. The mass of pure peptide was identified by electrospray MS. The composition of the peptide was verified by amino acid analysis and purity was estimated by analytical HPCL. The mass per peptide was measured by molecular mass analysis using SCIEX API Biomolecular Mass Analyzer (PE Applied BioSystems, Foster City, Calif.).

EXAMPLE 3

Pharmacological Binding

Determination of $IC_{50}$ for labeled peptides. Samples were prepared for $IC_{50}$ determination by dissolving 2–10 nmols of the sample into a final volume of 0.5 mL. In order to fully dissolve the peptide, the sample was reconstituted in 20 uL DMSO, vortexing well to ensure that all powder was completely dissolved, and then adding 0.48 mL of double distilled water. The stock solution was aliquoted to avoid repeated freezing and thawing of peptide. Unused aliquots were stored at −20° C. (protected from light) for a maximum of 24 hr.

Receptor binding was carried out on rat brain homogenate by Fluo-motilin or recombinant motilin (RB-HMOT) (Receptor Biology, Inc., Beltsville, Md.). Tests were conducted at least in duplicate with three repeats recommended at 5–7 test concentrations (from approximately $10^{-12}$–$10^{-3}$ M depending on the binding values). All assays used 2 nM MOT741 and 0.9 $\mu$l of the membrane preparation in a total volume of 40 $\mu$l. Data for native and labeled peptides were analyzed by non-linear curve fitting. This included statistical evaluation of fit and calculation of $IC_{50}$ and $K_i$ values (see, FIG. 2).

All references cited herein are hereby incorporated by reference.

Other embodiments are within the scope of the following claims.

What is claimed is:

1. A compound of the formula:

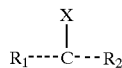

wherein $R_1$ is a light-emitting moiety and $R_2$ is a motilin peptide, fragment, derivative or analog thereof, wherein $R_2$ is comprised of the sequence Phe-Val-Pro-Ile-Phe-Thr-Tyr-Gly-Glu-Leu-Gln-Arg-Met-Gln-Glu-Lys-Glu-Arg-Asn-Lys-Gly-Gln (SEQ ID NO:1), and (C—X) is selected from the group consisting of C=O, C=S, CH (OH), C=C=O, C=NH, $CH_2$, CH (OR), CH (NR), CH(R), $CR_3R_4$, and C ($OR_3$) $OR_4$ where R, $R_3$, and $R_4$ are alkyl moieties or substituted alkyl moieties, and wherein $R_2$ is linked to (C—X) at an amino acid position selected such that the compound exhibits substantial biological activity in the presence of a receptor having affinity for motilin peptides.

2. The compound of claim 1, wherein $R_2$ is attached to $R_1$ via a linker moiety.

3. The compound of claim 2, wherein the linker moiety is selected from the group consisting of g-aminobutyric acid, glycine, beta-alanine, aminopentanoic acid, aminohexanoic acid, aminohepanoic acid, aminooctanoic acid, aminononanoic acid, aminodecanoic acid, aminoundecanoic acid, and aminododecanoic acid.

4. The compound of claim 1, wherein said amino acid position comprises the one of the C-terminal eight residues of the motilin peptide of SEQ ID NO:1.

5. The compound of claim 1, wherein said amino acid position comprises $Lys^{20}$ of the motilin peptide.

6. The compound of claim 1, wherein $R_1$ is bound, through C, to a region of said $R_2$ peptide which is not, involved in said biological activity.

7. The compound of claim 1, wherein said $R_2$ peptide binds to a human receptor.

8. The compound of claim 1, wherein said light-emitting moiety is selected from the group consisting of 4,4-difluoro-4-bora-3a,4a-diaza-s-indacene, fluorescein, FITC, Texas red, phycoerythrin, rhodamine, carboxytetramethylrhodamine, indopyras dyes, Cascade blue, coumarins, NBD, Lucifer Yellow, propidium iodide, dinitrophenol (DNP), lanthanide cryptates, lanthanide chelates, non-fluorescent dialdehydes which react with primary amines to form fluorescent isoindoles, dansyl, fluorescamine and dabcyl chloride, 5-((((2-iodoacetyl)amino)ethyl)amino) naphthalene-1-sulfonic acid, long lifetime dyes comprised of metal-ligand complexes (MLC) and derivatives thereof.

9. The compound of claim 1, wherein (C—X) is C=O or C=S.

10. The compound of claim 1, wherein said compound is a pharmaceutically acceptable salt or complex thereof.

11. A method for labeling a receptor having an affinity for a motilin peptide by contacting said receptor with the compound of claim 1.

12. A method for generating a biologically active compound of claim 1, comprising:

reacting $R_1$ and $R_2$ in an aqueous solution to form a mixture comprising the compound of claim 1 and secondary compounds having biological activities less than 0.25% of the biological activity of $R_2$—H in the presence of a receptor having affinity for motilin peptides;

contacting the mixture with a receptor for motilin peptides; and isolating from said mixture a light-emitting compound exhibiting substantial biological activity in the presence of said motilin peptide receptor.

13. The method of claim 12, wherein said isolating step comprises:

releasing said light emitting compound from said motilin peptide receptor; and isolating said light-emitting compound.

14. The method of claim 13, wherein said step of isolating said light-emitting compound includes selection by high pressure liquid chromatography.

15. A method for imaging cell receptor sites comprising contacting candidate cell receptor sites with a compound of claim 1, and detecting said bound compound as an indication of said cell receptor sites.

16. A method of cell sorting comprising contacting a population of candidate cells with a compound of claim 1, and isolating cells bound to said compound.

17. A method of flow cytometry comprising contacting a population of cells with a compound of claim 1 and detecting cells bearing receptors on their surfaces by detecting cells bound to said compound.

18. An assay method for evaluating a known or candidate motilin agonist or antagonist molecule for receptor binding selectivity, said method comprising bringing together a molecule, the compound of claim 1, and a motilin receptor preparation containing motilin receptors capable of binding motilin, and determining or measuring the ability of said molecule to compete against said compound for binding to said motilin receptor preparation.

19. An assay method for determining the presence or amount of a motilin receptor binding molecule in a test sample, said method comprising the steps of:

a) bringing together the test sample and a motilin receptor preparation containing motilin receptors capable of binding motilin;

b) measuring the ability of the test sample to compete against the compound of claim 1 for binding to the motilin receptor preparation; and c) comparing the amount of motilin receptor binding molecule in the test sample to the amount of motilin receptor binding in a control sample.

20. An assay method for screening cell lines, cells desegregated from tissue, or cell membrane preparations, to identify those cells that carry motilin receptors, said method comprising:

a) contacting test cell lines, cells desegregated from tissue, or cell membrane preparations with the compound of claim 1;

b) detecting an increase in fluorescent signal on said cell line, desegregated cell, or cell membrane preparation, compared to a negative control, an increase in fluorescent signal indicating that a motilin receptor is present in the cell.

21. A kit for identifying target compounds for the treatment of motilin-related disease, comprising:

a) at least one of the compounds of claim 1; and
b) a receptacle containing a motilin receptor preparation.

* * * * *

SEQUENCE LISTING

```
<160> NUMBER OF SEQ ID NOS: 3

<210> SEQ ID NO 1
<211> LENGTH: 22
<212> TYPE: PRT
<213> ORGANISM: Homo sapiens

<400> SEQUENCE: 1

Phe Val Pro Ile Phe Thr Tyr Gly Glu Leu Gln Arg Met Gln Glu Lys
1               5                   10                  15

Glu Arg Asn Lys Gly Gln
            20

<210> SEQ ID NO 2
<211> LENGTH: 22
<212> TYPE: PRT
<213> ORGANISM: Homo sapiens

<400> SEQUENCE: 2

Phe Val Pro Ile Phe Thr His Ser Glu Leu Gln Lys Ile Arg Glu Lys
1               5                   10                  15

Glu Arg Asn Lys Gly Gly
            20
```

```
<210> SEQ ID NO 3
<211> LENGTH: 22
<212> TYPE: PRT
<213> ORGANISM: Homo sapiens

<400> SEQUENCE: 3

Phe Val Pro Ile Phe Thr Tyr Gly Glu Leu Gln Arg Met Gln Glu Lys
1               5                   10                  15

Glu Arg Asn Lys Gly Gln
            20
```